US008241324B2

(12) United States Patent
Babaev et al.

(10) Patent No.: US 8,241,324 B2
(45) Date of Patent: Aug. 14, 2012

(54) ULTRASONIC VASCULAR CLOSURE DEVICE

(76) Inventors: Eilaz Babaev, Minnetonka, MN (US); Adolfo Menendez, Woodbury, MN (US)

( * ) Notice: Subject to any disclaimer, the term of this patent is extended or adjusted under 35 U.S.C. 154(b) by 1141 days.

(21) Appl. No.: 12/041,101

(22) Filed: Mar. 3, 2008

(65) Prior Publication Data

US 2009/0222037 A1 Sep. 3, 2009

(51) Int. Cl.
*A61B 17/03* (2006.01)
(52) U.S. Cl. ............ 606/213; 606/214; 606/232; 601/2; 601/3
(58) Field of Classification Search .................. 600/407, 600/437, 459–467; 606/213, 232, 72, 200, 606/19, 22, 32, 139, 144, 148; 604/24, 19, 604/22; 601/2–3; 128/898; 424/422–424
See application file for complete search history.

(56) References Cited

U.S. PATENT DOCUMENTS

| | | | |
|---|---|---|---|
| 4,744,364 A | 5/1988 | Kensey | |
| 4,890,612 A | 1/1990 | Kensey | |
| 4,929,246 A | 5/1990 | Sinofsky | |
| 5,016,615 A * | 5/1991 | Driller et al. ...................... 601/2 |
| 5,312,435 A | 5/1994 | Nash et al. | |
| 5,383,896 A | 1/1995 | Gershony et al. | |
| 5,415,657 A | 5/1995 | Taymor-Luria | |
| 5,507,738 A | 4/1996 | Ciervo | |
| 5,613,974 A | 3/1997 | Andreas et al. | |
| 5,626,601 A | 5/1997 | Gershony et al. | |
| 5,676,689 A | 10/1997 | Kensey et al. | |
| 5,810,810 A | 9/1998 | Tay et al. | |
| 5,868,778 A | 2/1999 | Gershony et al. | |
| 5,935,144 A * | 8/1999 | Estabrook ..................... 606/169 |
| 6,045,570 A | 4/2000 | Epstein et al. | |
| 6,296,657 B1 | 10/2001 | Brucker | |
| 6,325,789 B1 | 12/2001 | Janzen et al. | |
| 6,464,660 B2 * | 10/2002 | Brisken et al. ................... 604/22 |
| 6,562,059 B2 | 5/2003 | Edwards et al. | |
| 6,569,185 B2 | 5/2003 | Ungs | |
| 6,656,136 B1 | 12/2003 | Weng et al. | |
| 6,705,323 B1 * | 3/2004 | Nikolchev et al. ............ 128/830 |
| 6,743,195 B2 | 6/2004 | Zucker | |
| 6,780,197 B2 | 8/2004 | Roe et al. | |
| 6,942,674 B2 | 9/2005 | Belef et al. | |
| 7,008,441 B2 | 3/2006 | Zucker | |
| 7,060,084 B1 | 6/2006 | Loshakove et al. | |
| 7,115,127 B2 | 10/2006 | Lindenbaum et al. | |
| 7,169,168 B2 | 1/2007 | Muijs Van De Moer et al. | |
| 7,223,266 B2 | 5/2007 | Lindenbaum et al. | |
| 7,318,933 B2 | 1/2008 | Hnojewyj | |
| 7,320,692 B1 | 1/2008 | Bender et al. | |
| 7,331,981 B2 | 2/2008 | Cates et al. | |
| 7,335,220 B2 | 2/2008 | Khosravi et al. | |
| 7,344,544 B2 | 3/2008 | Bender et al. | |
| 2002/0029051 A1 * | 3/2002 | Callister et al. ............... 606/157 |
| 2003/0125645 A1 * | 7/2003 | Rabiner et al. ..................... 601/2 |

(Continued)

*Primary Examiner* — Corrine M McDermott
*Assistant Examiner* — Mark Mashack (57) ABSTRACT

The present invention relates to the use of a low frequency ultrasonic device for the delivery and activation of collagen based foam sealants to a human and/or animal patient for sealing puncture wounds in vascular tissues. The ultrasonic vascular closure device comprises an ultrasonic generator, an ultrasound transducer, a chamber containing a foam sealant, a transducer tip, a radiation surface, an orifice located at the distal end of the chamber. The foam sealant is ejected into a puncture wound and activated with ultrasonic waves emitting from the radiation surface. The ultrasonic waves induce vibrations within the foam sealant, slightly warming the foam sealants to assist the rapid sealing the puncture. The ultrasonic waves also provide and anesthetic effect for the pain and discomfort from the puncture site.

20 Claims, 5 Drawing Sheets

U.S. PATENT DOCUMENTS

| | | |
|---|---|---|
| 2003/0176791 A1* | 9/2003 | Rabiner et al. ............... 600/439 |
| 2004/0116921 A1* | 6/2004 | Sherman et al. ............... 606/41 |
| 2004/0255958 A1* | 12/2004 | Harrington et al. ........... 128/898 |
| 2005/0085855 A1 | 4/2005 | Forsberg |
| 2006/0015108 A1* | 1/2006 | Bonutti ............................ 606/72 |
| 2006/0212055 A1* | 9/2006 | Karabey et al. ............... 606/158 |
| 2006/0217744 A1 | 9/2006 | Bender et al. |
| 2006/0235470 A1* | 10/2006 | Bonutti et al. ................. 606/232 |
| 2007/0032825 A1* | 2/2007 | Bonutti et al. ................. 606/232 |
| 2007/0049967 A1 | 3/2007 | Sibbitt, Jr. et al. |
| 2007/0083231 A1 | 4/2007 | Lee |
| 2007/0083232 A1 | 4/2007 | Lee |
| 2007/0179379 A1 | 8/2007 | Weng et al. |
| 2007/0239078 A1* | 10/2007 | Jaeb ................................. 601/2 |
| 2007/0276435 A1 | 11/2007 | Yassinzadeh et al. |
| 2007/0293888 A1 | 12/2007 | Harren et al. |
| 2008/0039727 A1 | 2/2008 | Babaev |
| 2008/0039745 A1 | 2/2008 | Babaev |
| 2008/0051693 A1 | 2/2008 | Babaev |
| 2008/0097251 A1 | 4/2008 | Babaev |
| 2008/0097479 A1 | 4/2008 | Boehlke et al. |

* cited by examiner

ULTRASONIC VASCULAR CLOSURE DEVICE

BACKGROUND OF THE INVENTION

The present invention relates to a low frequency medical device and method for the sealing of tissue puncture wounds after surgical procedures.

With improvement in medical devices and procedures, it is increasingly becoming possible to avoid the trauma and complications caused by open surgery using various transcatheter techniques. Some examples of these procedures include; angiography, percutaneous transluminal coronary angioplasty, stenting, atherectomy and catheter ablation. These new methods are being developed because they offer significant benefits with respect to patient recovery, potential complications and cost. The early discharge of patients undergoing these elective and interventional procedures hinges on the lack of bleeding complications at the access site after the procedure sheath is removed from the artery. The size of the access route, coupled with the routine administration of anticoagulants, creates a strong need to stop bleeding at the puncture site as quickly as possible. However, hemostasis must be achieved without producing clotting in the vessel just treated in order to prevent a potentially fatal myocardial infarction or thrombosis.

Simple compression is currently the standard of care for managing vascular access sites following interventionial cases. Compression includes the use of hand pressure, clamps and/or sand bags. To begin with, anticoagulant therapy typically has to be discontinued up to four hours prior to vascular closure in order to permit the patient's clotting capability to improve. During this period the patient must remain immobilized to prevent bleeding with the sheath in place. Upon sheath removal a nurse or technician holds direct pressure on the site for at least 30 minutes until thrombus forms to seal the access site. Once hemostasis has been achieved the patient must remain motionless for a period of time that may range from 4 to 24 hours to minimize the risk of dislodging the clot. Furthermore, the direct pressure necessary to close the vessel puncture may restrict blood flow within the vessel itself, causing unwanted complications to the patient.

To overcome the problems associated with manual compression, the use of a variety of alternative methods have been developed. These systems commonly known include heat sealing, lasers, suture based systems, or various types of plugs or glues. Plugs may be made in many different shapes and may be created from a variety of materials. No matter what the material or the shape of the plug, accurate placement of the plug is desirable. Placement is particularly import with prior art plug systems which use some portion of the patient's blood to form a clot or other obstructions.

Prior art closure systems include devices such as the one described in U.S. Pat. No. 5,626,601 to Gershoney. This particular system uses a balloon which can be inflated to prevent the closure material from entering the vessel. Once the plug material has been injected into the vascular access site and partially solidifies, the balloon is deflated and pulled through the plug material. Another prior art closure device invented by Kensey and described in U.S. Pat. No. 5,676,689, uses a biodegradable backstop to prevent a plug from entering the vessel.

Prior art references that describe cauterization sealing of the vessel opening include U.S. Pat. Nos. 4,929,246; 5,810,810; and 5,415,657, which disclose the use of a laser or of radio-frequency (RF) energy that is transmitted to the blood vessel through a catheter to thermally fuse or weld the punctured tissue together. U.S. Pat. No. 6,656,136 to Weng et al, describe the use of high intensity focused ultrasound to cauterize the wound opening.

The prior art devices do not effectively resolve the problems associated with alternative mechanisms to the use of compression for vascular sealing and do not provide the benefits of the present invention as described below.

SUMMARY OF THE INVENTION

Apparatus and methods in accordance with the present inventions may resolve many of the needs and shortcomings discussed above and will provide additional improvements and advantages as will be recognized by those skilled in the art upon review of the present disclosure.

The present inventions provide an ultrasonic vascular closure device for sealing a patient's tissue wound with a collagen material. A specific application for use in vascular sealing is described in detail as an exemplary embodiment of the invention. However, the device has applicability to the sealing of tissue puncture wounds generally. The present invention does not rely on the patient's blood to provide the seal between the plug and the tissue. Rather, the application of ultrasound to the collagen creates a matrix between the tissue and the plug. Therefore, extending hospital stay time for anticoagulant dissipation is not required. Furthermore, the time required to complete the procedure of the present invention can be completed in 5 to 10 minutes or less, rather than the 30 minutes to several hours required for compression techniques. The reduction in patient stay length and staff time can result in considerable cost savings. Furthermore, there is considerable less likelihood of the wound reopening after the patient is released, reducing costs as well as reducing risks to patient recovery from the procedure.

The present invention includes injecting a collagen based foam sealant into a tissue puncture wound. The foam sealant is then activated with an ultrasonic device to seal the wound. The ultrasonic device includes an ultrasound generator, a movable ultrasound transducer, a transducer tip at the distal end of the ultrasound transducer, a radiation surface at the distal end of transducer tip, a cavity and a vascular closure device head. A transducer housing is fixedly attached to the ultrasound transducer. A transducer tip may be located at the distal end of the ultrasound transducer. The distal end of the transducer tip is configured as a radiation surface.

The ultrasonic device also has a body to contain the transducer housing and proximal portions of the transducer tip; the body is slideably attached to a dispenser portion for ejecting the foam sealant from the chamber, through an orifice and into a tissue puncture wound. A dispenser portion forms the chamber that contains at least portions of the transducer tip including a radiation surface inside the chamber. Sliding the dispenser portion into the body reduces the volume of the chamber. The interface between the body and the dispenser portion is designed with a sealing function to prevent leakage of the foam sealant.

An orifice is located at the distal end of the chamber. As an alternative embodiment to using the foam sealant alone, the chamber may also contain a thread as well as an anchor. When used, the anchor is placed in the chamber, transported to the distal end of the puncture and then ejected from the chamber through the orifice. The thread is preferably attached to the anchor and serves as a means to keep the anchor in place as well as to provide a mechanism to keep the anchor against the puncture. The thread may also be used to provide a structure reinforcing the foam sealant as the foam sealant is being ejected from the chamber, as it is being activated and after sealing to hold the anchor and foam sealant in place. Preferably all of the material of the foam sealant, anchor and thread are biodegradable or bioabsorbable materials and will eventually be replaced by tissue growth as the wound heals.

The ultrasound energy generated at the ultrasound transducer is transmitted through the transducer tip causing; vibration of the radiation surface. The ultrasound energy is then emitted from the radiation surface. As the chamber is collapsed, the radiation surface moves through the chamber toward the orifice and may extend through the orifice for optimal activation of the ejected foam sealant.

Other features and advantages of the invention will become apparent from the following detailed description and from the claims.

DETAILED DESCRIPTION OF THE INVENTION

The figures generally illustrate embodiments of an ultrasonic device 10 including aspects of the present inventions. The particular exemplary embodiments of the ultrasonic device 10 illustrated in FIGS. 1-4 have been chosen for ease of explanation and understanding of various aspects of the present invention. These illustrated embodiments are not meant to limit the scope of coverage but instead to assist in understanding the context of the language used in this specification and the appended claims. Accordingly, many variations from the illustrated embodiments may be encompassed by the appended claims.

Figure 1:
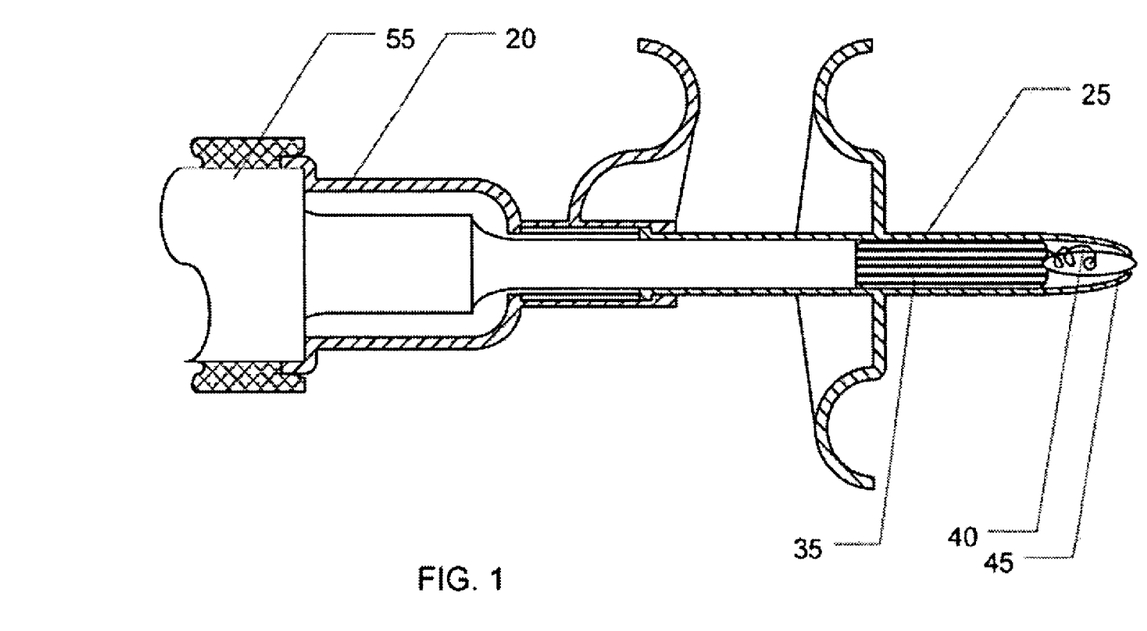
FIG. 1 illustrates a cut away side view of aspects of an embodiment of an ultrasonic device according to the present inventions.
Figure 2:
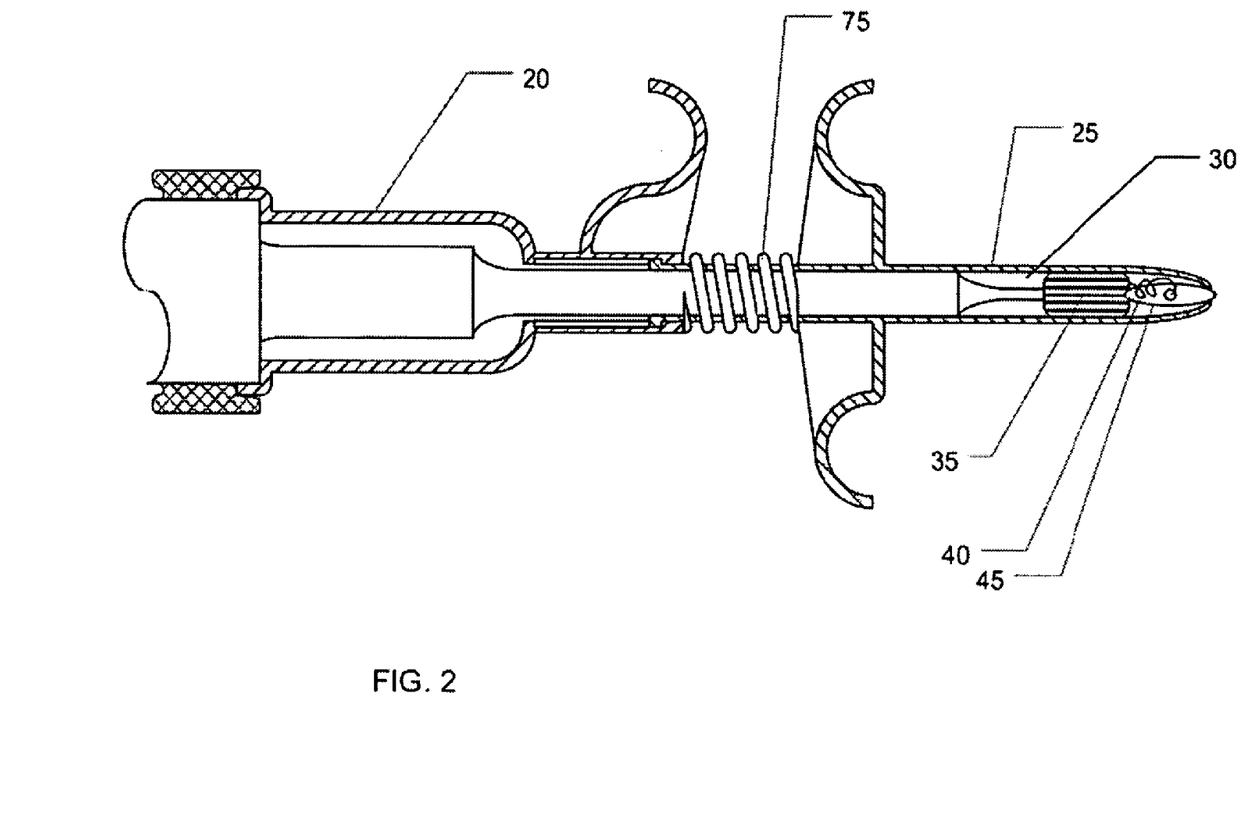
FIG. 2 illustrates a cut away side view of aspects of an embodiment of an ultrasonic device according to the present inventions.

The present invention provides an ultrasonic device 10 for sealing a patient's tissue puncture wounds using ultrasound radiation. As illustrated in FIGS. 1 and 2, the ultrasonic device 10 includes an ultrasound generator connected to an ultrasound transducer 50 through a releasable connector 70.

Figure 3:
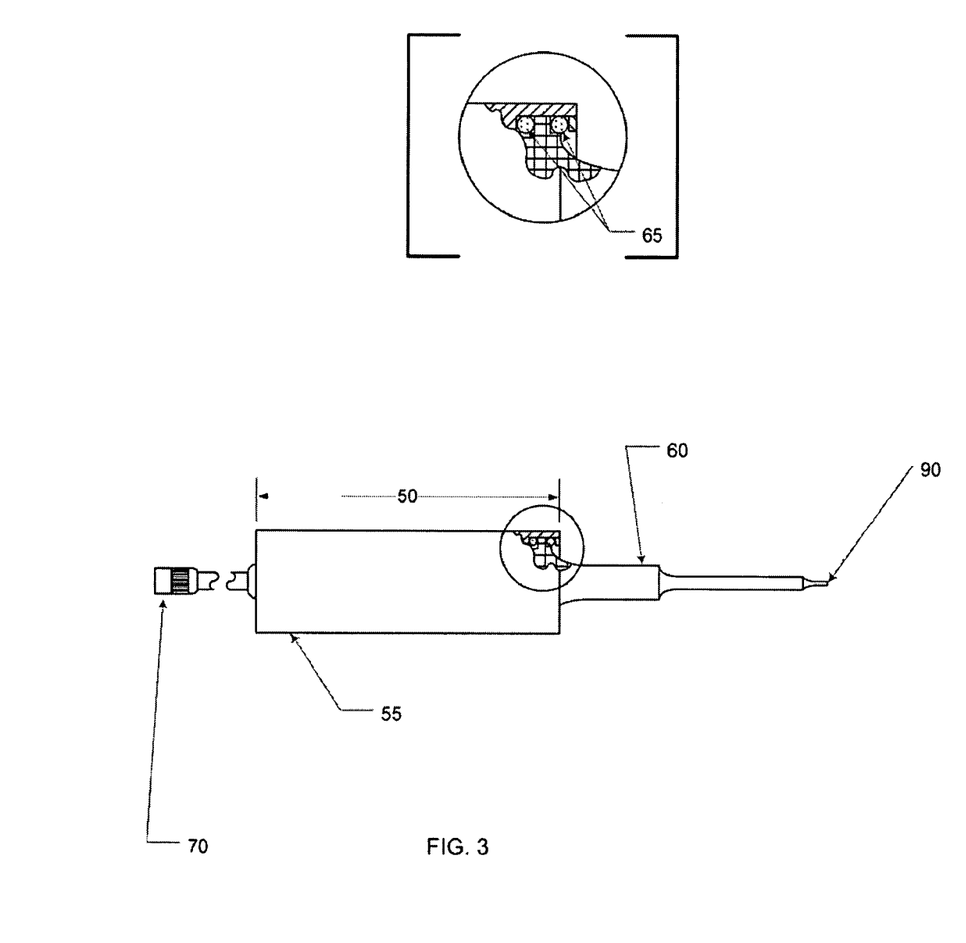
FIG. 3 illustrates a side view of the ultrasonic tip of the ultrasonic device according to the present invention.

A transducer housing 55 is fixedly attached to the ultrasound transducer 50. The transducer housing 55 constructed preferably of aluminum, may also be constricted of titanium alloy, stainless steel or other material as known in the art. Preferably, as shown in FIG. 3, the vibration transmissions to the transducer housing 55 from the ultrasound transducer 50 are dampened through an isolation seal 65 using an assembly of O-rings which also provides a means to allow expansion of the ultrasound transducer 50 independently from the transducer housing 55.

A transducer tip 60 may be located at the distal end of the ultrasound transducer 50. The distal end of the transducer tip 60 is configured as a radiation surface 90. The ultrasound energy generated by the transducer 50 is transmitted to radiation surface 90 by ultrasonic vibrations induced in tip 60. Upon reaching radiation surface 90, the vibrations are released as ultrasonic waves carrying ultrasonic energy. Accordingly, the ultrasound energy generated by transducer 50 is emitted from radiation surface 90 into chamber 30. A dispenser portion 25 forms a chamber 30 which is variable in size and contains at least portions of the transducer tip 60 including the radiation surface 90 as shown in FIGS. 1 and 2.

An orifice 95 is located at the distal end of the chamber 30. The chamber 30 contains a foam sealant 35 which is ejected from the chamber into the would through the orifice 95. Alternatively, as described below, the chamber 30 may also contain a thread 40 and an anchor 45.

Foam sealant 35 may be comprised of fiber forming proteins such as, but not limited to, collagen and/or elastin. In combination or in the alternative, foam sealant 35 may comprise glycoproteins associated with extracellular matrices such as, but not limited, laminin, entactin, and/or fibronectin. The foam sealant 35 is activated by the ultrasonic radiation energy to seal the wound. The ultrasonic energy released into chamber 30 enters foam sealant. As the energy propagates through the sealant 35, the sealant begins to heat and vibrations are induced in the sealant. Consequently, the propagation of ultrasonic energy released from radiation surface 90 through sealant 35 activates sealant 35 by increasing its kinetic energy. Activating sealant 35 may make it easier to eject through orifice 95. In combination or in the alternative, activation of sealant 35 may increase the degree to which the sealant diffuses into the surrounding tissue. Increasing the diffusion of the sealant into the surrounding tissue may better anchor the plug formed by the sealant. Sealant that has into the surrounding tissue may bind to integrins on the cells and/or various components of the extracellular matrix of the surrounding tissue. Binding to the cells and/or extracellular matrix of the surrounding tissue, the plug formed by the sealant becomes anchored within wound. Anchoring the plug within the wound may increase the integrity of plug. It is also possible that activation of the sealant may induce other reactions that better secure and/or increase the stability of the resulting plug.

In combination or in the alternative, activation of the sealant 35 may induce the ionization, oxidation, generation of free radical and/or other chemical modifications within the sealant 35. Chemically modifying sealant 35 may produce desirable effects such as increasing the sealant's integrity and/or the strength of its interactions with the tissue surrounding the wound. For example, the activation of a foam sealant comprised of collagen may lead to an increase prevalence of hydroxyproline and/or hydroxylysine with the collagen molecules. Increasing the prevalence of hydroxyproline may increase the amount of hydrogen bonding between the strands and/or surrounding tissue. Likewise, increasing the prevalence of hydroxylisne may increase the amount of covalent bonding between the collagen strands and/or surrounding tissue. Increasing the amount of binding between the collagen strands of the sealant and/or the tissue may better secure and increase the structure integrity of the plug produced from foam sealant 35.

The device also has a body 20 to contain the transducer housing 55 and proximal portions of the transducer tip 60; the body 20 is slideably attached to a dispenser portion 25. As the dispenser portion 25 moves into the body 20, the chamber 30 decreases in volume thereby ejecting the foam sealant 35 from the chamber 30, through the orifice 95 and into a tissue puncture wound. The interface between the body 20 and the dispenser portion 25 is designed to include a sealing means to prevent leakage of the foam sealant 35 past the adjacent surfaces. This surface may be sealed by conventional means such as flexible seals or by providing close tolerances between the surfaces.

Figure 4A:
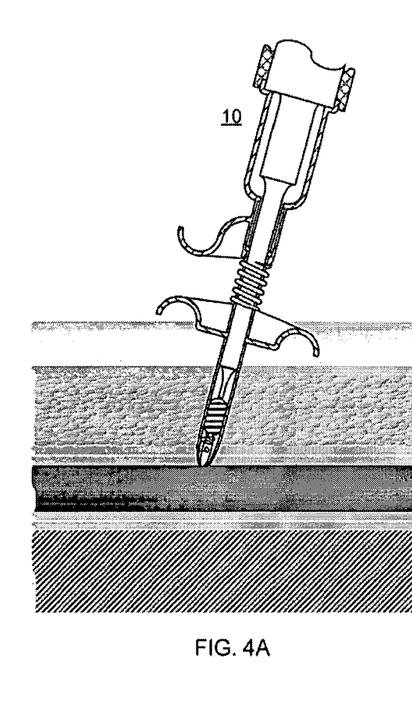
FIG. 4A through 4E show several sequential views of selected stages for a method of use according to the present invention.
Figure 4B:
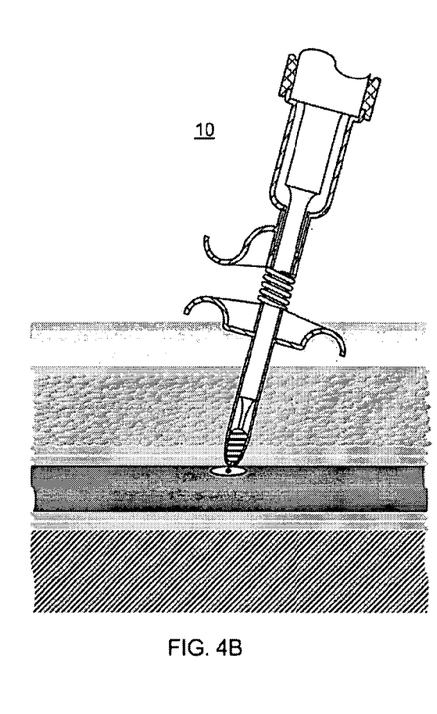
Figure 4C:
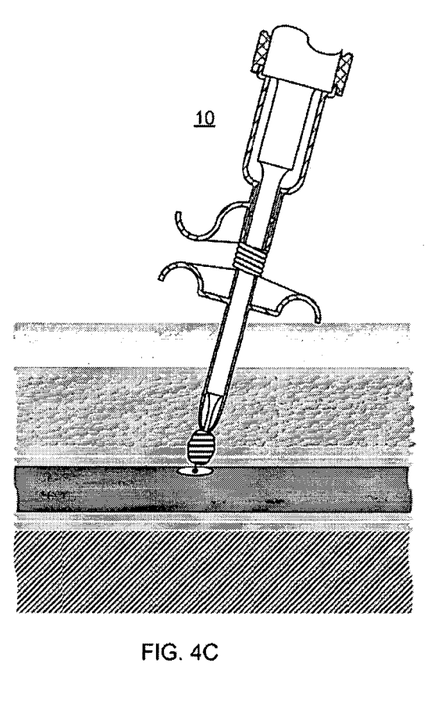

With reference to FIGS. 4A-4E, the steps for sealing a tissue puncture wound are shown. As shown in FIG. 4A, the proximal end of the dispenser portion 25 containing the orifice 95 is positioned near the tissue puncture wound. In vascular repair, this positioning can be assisted with or without various known scanning techniques which can be augmented through the use of known contrast agents. Following positioning of the device, as shown in FIG. 4B the anchor 45, when used, is placed within the vascular lumen to be sealed at the distal end of the puncture wound. The foam sealant 35 and any other contents within the chamber 30 is then ejected into the proximity of the tissue puncture wound as shown in FIG. 4C. Injection is accomplished by moving the dispenser portion 25 in the body 20 to decrease the volume of chamber 30.

Preferably, a spring 75 is biased between the body 20 and the dispenser portion 25. As the dispenser portion 25 is slid into the body 20 the size of the chamber 30 is correspondingly reduced. As the chamber size decreases the contents of the chamber 30 which may include the foam sealant 35, a thread 40 and the anchor 45 are ejected from the chamber 30. Upon release of the compressive forces necessary to bias the spring 75 automatically returns the chamber 30 back to its original size. Depressing the transducer to eject the foam sealant 35 can be accomplished manually or through the use of a motorized drive.

Figure 4D:
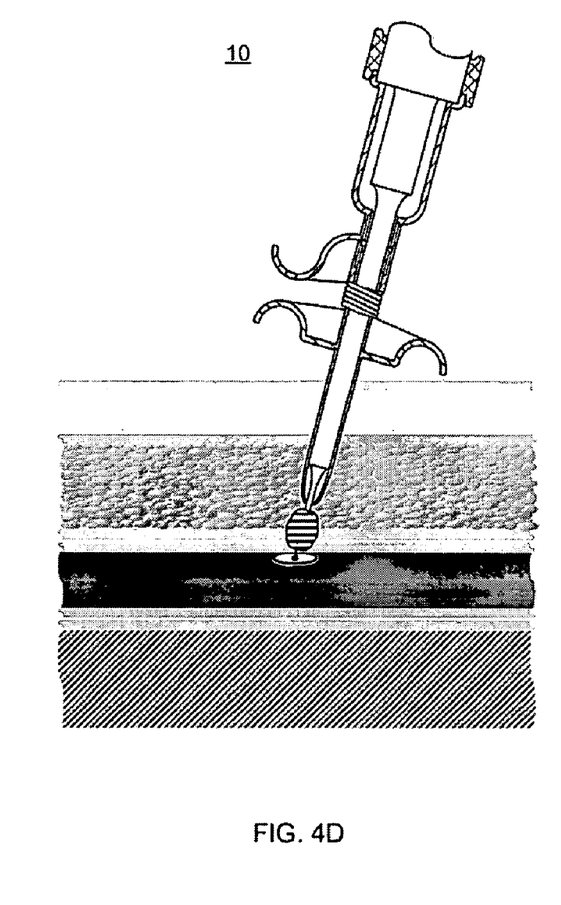

As the dispenser portion 25 is moved within the body 20 to collapse the chamber 30, the radiation surface 90 which is fixed to the body 20 moves toward the orifice 95. As shown in FIG. 4D, the foam sealant 35 is then ejected from the chamber 30 and the radiation surface 90 may travel through the opening of the orifice 95. The foam seal 35 is activated with the ultrasound emitted from the radiation surface 90 and the device is withdrawn. The activation can take from several seconds to a few minutes depending on the amount and composition of sealant 35, size of the puncture and chrarcteristics of the ultrasound applied.

Figure 4E:
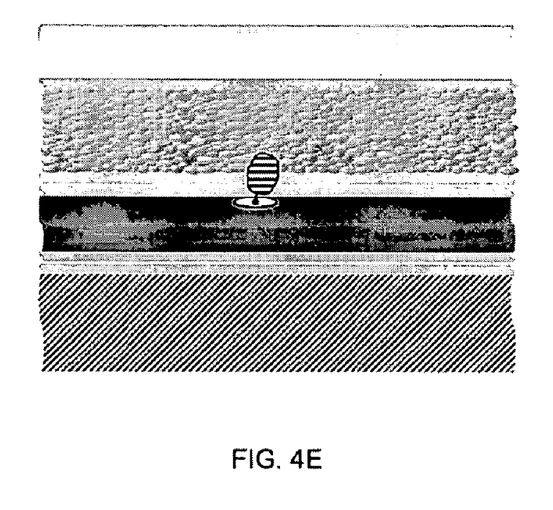

FIG. 4E shows the sealed puncture with the anchor 45, foam seal 35 and thread 40 left in place. These elements are preferably fabricated from bioabsorbable or biodegradable materials and will be replaced with natural tissue as the wound heals.

When used, the anchor 45 may be fixedly attached to the thread 40, all of which are placed or loaded next to the orifice 95 within the chamber 30 of the dispenser portion 25. The anchor 45 will have a compact configuration for placement in the chamber and discharge through the orifice 95. After discharge, the anchor 45 expands to a final configuration that is large enough so that it will not readily pass back through the orifice 95. The anchor is preferably located within the vessel lumen to serve as a plug device to prevent the foam sealant 35 from dispersing into the vessel. The anchor 45 may be a of a variety of known devices that include compressible materials that expand when released, materials that swell when wetted, or may include rigid devices that can be collapsed, translated, folded and/or rotated for passing through the orifice 95, but will unfold, expand, translate and/or rotate when ejected into the lumen. The anchor 45, thread 40 and/or foam sealant 35 are preferably constructed of biodegradable or absorbable materials. Alternatively, the thread 40 may be semi rigid wire or wire bundle that breaks free of the anchor 45 and pulls through the foam sealant 35. The anchor 45, thread 40 and/or foam sealant 35 may have a therapeutic coating to assist healing.

The anchor 45 is preferably attached to a thread 40. The thread 40 is ejected with the anchor 45 and foam sealant 35. The thread 40 is may be used to pull the anchor 45 firmly against the interior wall of the lumen. The thread 40 may function as a scaffold for sealant 35. The thread 40 also serves to hold the anchor 45 in place and to prevent premature dislodgement of the anchor 40. Preferably, the thread 40 may be composed of a biodegradable suture material.

The foam sealant 35 preferably consists of a biodegradable material that is activated with ultrasound. The foam sealant 35 is placed in the chamber 30 and transported to the tissue puncture site. Exposing the foam sealant 35 to ultrasound energy may be initiated while the foam sealant 35 is within the chamber 30. Doing, this may assist in ejecting of the foam sealant 35 into the wound. Furthermore, the foam sealant 35 serves as a coupling media to transfer the ultrasound waves into the tissue of the patient.

Preferably, the foam sealant 35 is ejected from the chamber 30 and then activated. Ultrasonic stimulation of the foam sealant 35 and tissue puncture wound provides numerous beneficial effects. The ultrasonic energy provides activation of the foam sealant some heat, vibration and stimulation. It is important to note that the low intensity ultrasound does not seal the puncture through cauterization with the associated problems and risks of tissue damage and other complications associated with high energy delivery. Instead, the low frequency ultrasound produces low levels of heat and vibration only sufficient to quickly activate the foam sealant 35. This prevents bleeding without relying on the clotting characteristics of the patient's blood, reducing the likelihood of a potentially dangerous thrombosis. Alternatively, the thread 40 may be semi rigid wire or wire bundle that breaks free of the anchor 45 and pulls through the foam sealant 35.

In addition, low frequency ultrasound provides an independent beneficial anesthetic effect during its application which enhances patient comfort during the procedure.

The ultrasound generator has a preferred power input in the range of 50 watts to 130 watts. A power source such as a battery or AC supply may be connected to the ultrasound generator to provide electrical power to the ultrasound generator for generation of the electrical signal. The ultrasound generator may produce an electrical signal having various frequencies. The ultrasound generator may be configured to produce an electrical signal having a preselected constant signal frequency or may be configured to produce an electrical signal having a controllable variable signal frequency. The electrical signal then may be used to drive the ultrasound transducer 50 which may be a sinusoidal wave, square wave, triangular wave, trapezoidal wave, or any combination thereof.

The ultrasound transducer 50 converts the electrical signal supplied by the ultrasound generator into a mechanical oscillation. The transducer tip 60 may be mechanically connected to the ultrasound transducer 50 so that the mechanical oscillation may be transmitted to the transducer tip 60 by the ultrasound transducer 50 to excite the transducer tip 60. The mechanical oscillation has an oscillation frequency that generally corresponds to the signal frequency supplied to the ultrasound transducer 50 by the ultrasound generator.

The ultrasound transducer utilized may be capable of vibrating in resonance at a frequency of between 16 kHz and 20 mHz, preferably 30 kHz. The ultrasonic vibrations traveling down the ultrasound transducer 50 may have an amplitude of approximately 1 to 300 microns with a preferred wavelength of 60 microns.

The ultrasound tip 60 may be integral or removable from the ultrasound transducer 50. Preferably, the ultrasound tip 60 is constructed from titanium alloy although stainless steel and other materials know in the art are also acceptable. Preferably the ultrasound tip 60 can be sterilized through convention means and preferably it is autoclavable. The ultrasound tip 60 is sized in proportion to its use. Preferably the ultrasound tip 60 has a maximum size between 0.1 to 0.5 cm for the distal end that enters the puncture. The ultrasound tip 60 distal end may be further restricted to a diameter preferably in the range of 0.05 to 0.3 cm for the portion that includes the radiation surface 90.

The ultrasonic waves traveling down the ultrasound tip 60 are emitted through the radiation surface 90. The radiation surface 90 of the present invention may be formed in a variety of shapes, such as, but not limited to flat, angled, conical, concave or convex and/or any combination thereof. A flat surface may be preferred for embodiments that prefer production of parallel ultrasound waves rather than focusing or dispersing of the ultrasound waves.

The radiation surface 90 may be positioned within the chamber as shown in FIG. 4A or the radiation surface 90 may be urged through the orifice to a position external to the chamber as represented in FIG. 4D. Energizing the radiation surface 90 internal to the chamber utilizes the foam sealant 35 as a coupling medium for the ultrasound waves. This may be advantageous when the ultrasound energy may be used to activate the therapeutic agent either directly or indirectly through oxidation, ionization and/or, the production of free radicals and/or ozone. The potential for ultrasound to produce cavitation and micro-streaming can be utilized for some embodiments.

Moving the ultrasound tip 60 and the radiation surface 90 within the chamber 30 assists with ejecting the foam sealant 35 from the chamber. The foam sealant 35 may be activated with the radiation surface 90 moved through the chamber 30 and the orifice 95 to a position external to the dispenser portion 25. The foam sealant 35 is then activated with the low level ultrasonic energy to allow the foam sealant 35 to rapidly form a dependable seal of the puncture wound. As an added benefit, the ultrasonic waves may be used to activate a therapeutic agent, in addition, the ultrasonic waves themselves provide anesthetic effects as they interact with the nerve tissue adjacent to the wound.

Although specific embodiments have been illustrated and described herein, it will be appreciated by those of ordinary skill in the art that any arrangement that is calculated to achieve the same purpose may be substituted for the specific embodiments. It is to be understood that the above description is intended to be illustrative and not restrictive. The disclosed steps of the methods are not intended to be restricted to the order listed. Combinations of the above embodiments and; other embodiments will be apparent to those having skill in the art upon review of the present disclosure. The scope of the present invention should be determined with reference to the appended claims, along with the full scope of equivalents to which such claims are entitled.

We claim:

1. An ultrasonic device for sealing puncture wounds comprising:
    an ultrasound generator;
    an ultrasound transducer connected to the ultrasound generator;
    a transducer tip attached to the ultrasound transducer;
    a radiation surface formed at a distal end of the transducer tip;
    a body containing the ultrasound transducer;
    the body being slideably attached to a dispenser portion the dispenser portion forming a chamber;
    the radiation surface within the chamber;
    an orifice at the distal end of the chamber; and
    the dispenser portion holding a foam sealant for ejecting from the dispenser portion wherein the foam sealant is activated by the ultrasound energy emitted from the radiation surface changing the number of electrons within the sealant.

2. The ultrasonic device of claim 1 wherein the foam sealant comprises a biodegradable collagen.

3. The ultrasonic device of claim 1 further comprising a transducer housing surrounding the ultrasound transducer and an isolation seal between the ultrasound transducer and the ultrasound housing.

4. The ultrasonic device of claim 1 further comprising a spring biasing the dispenser portion.

5. The ultrasonic device of claim 1 further comprising a fluid seal between the body and the dispenser portion.

6. The ultrasonic device of claim 1 further comprising an anchor within the chamber, the anchor being dischargeable through the orifice.

7. The ultrasonic device of claim 1 wherein the chamber contains a therapeutic agent.

8. The ultrasonic device of claim 1 wherein the chamber contains a thread.

9. The ultrasonic device of claim 1 wherein the shape of the radiation surface is flat.

10. The ultrasonic device of claim 1 wherein the shape of the radiation surface is selected from the group consisting of conical, concave and convex.

11. The ultrasonic device of claim 1 wherein the foam sealant is in transferred from the chamber to a tissue puncture wound.

12. The ultrasonic device of claim 1 wherein ultrasound energy emitted from the radiation surface assist the transfer of the foam sealant from a chamber through the orifice.

13. The ultrasonic device of claim 1 wherein the radiation surface emits ultrasound waves at an amplitude within a range of 1 micron to 300 microns.

14. The ultrasonic device of claim 1 wherein the radiation surface emits ultrasound waves at a wavelength within a range of approximately 60 microns.

15. The ultrasonic device of claim 1 wherein the radiation surface emits ultrasound waves at a frequency between 16 kHz and 20 mHz.

16. The ultrasonic device of claim 1 wherein the radiation surface emits ultrasound waves at a frequency of approximately 30 kHz.

17. An ultrasonic device for sealing puncture wounds comprising:
    an ultrasound generator;
    an ultrasound transducer connected to the ultrasound generator;
    a transducer tip attached to the ultrasound transducer;
    a radiation surface formed at a distal end of the transducer tip;
    a body containing the ultrasound transducer;
    the body being slideably attached to a dispenser portion;
    a chamber within the dispenser portion holding a foam sealant for ejecting from the dispenser portion;
    the radiation surface within the chamber;
    an orifice positioned at a distal end of the chamber; and
    the radiation surface being moveable through the orifice wherein the foam sealant is activated by the ultrasound energy emitted from the radiation surface changing the number of electrons within the sealant.

18. The ultrasonic device of claim 17 wherein the foam sealant is a coupling medium for the ultrasound waves emanating from the radiation surface.

19. The ultrasonic device of claim 17 wherein the foam sealant also comprises a therapeutic agent activated by ultrasound energy emitted from the radiation surface.

20. The ultrasonic device of claim 17 also having a means for focusing ultrasound waves emanating from the radiation surface.

* * * * *